United States Patent [19]

Ichinohe et al.

[11] Patent Number: 5,705,665
[45] Date of Patent: Jan. 6, 1998

[54] ORGANIC SILICON COMPOUNDS AND PROCESS OF MAKING

[75] Inventors: Shoji Ichinohe; Hideyoshi Yanagisawa; Masayuki Takahashi, all of Gunma-ken, Japan

[73] Assignee: Shin-Etsu Chemical Co., Ltd., Tokyo, Japan

[21] Appl. No.: 766,275

[22] Filed: Dec. 13, 1996

[30] Foreign Application Priority Data

Dec. 15, 1995 [JP] Japan .................................. 7-347893

[51] Int. Cl.$^6$ ...................... C07F 7/08; C07F 7/18
[52] U.S. Cl. .......................................................... 556/428
[58] Field of Search ............................................. 556/428

[56] References Cited

U.S. PATENT DOCUMENTS

| | | | |
|---|---|---|---|
| 4,005,117 | 1/1977 | Heckert et al. | 556/428 X |
| 4,005,119 | 1/1977 | Heckert et al. | 556/428 X |
| 4,006,176 | 2/1977 | Heckert et al. | 556/428 X |
| 5,068,380 | 11/1991 | Meguriya et al. | 556/428 |

*Primary Examiner*—Paul F. Shaver
*Attorney, Agent, or Firm*—Millen, White, Zelano & Branigan, P.C.

[57] ABSTRACT

Organic silicon compounds having an alkoxy group at one end and an alkali metal salt of sulfonic acid or sulfuric acid at the other end are novel. They can be obtained by effecting hydrosilylation reaction between an alkoxyhydro-silane and a compound having an alkenyl group at one end and an alkali metal salt of sulfonic acid or sulfuric acid at the other end. They are useful as a modifier and surface treating agent.

10 Claims, 2 Drawing Sheets

ORGANIC SILICON COMPOUNDS AND PROCESS OF MAKING

BACKGROUND OF THE INVENTION

1. Field of the Invention

This invention relates to novel organic silicon compounds having a sulfonate group in their molecule which are useful as a modifier for composite materials of organic resins and inorganic materials and a surface treating agent for inorganic materials as well as a process for preparing the same.

2. Prior Art

A variety of organosilane compounds are known in the art as a modifier for composite materials of organic resins and inorganic materials and a surface treating agent for inorganic materials. It would be advantageous to have organic silicon compounds with which inorganic materials can be treated to be hydrophilic.

Compounds having sulfonic acid or sulfuric acid or a salt thereof in a molecule are known. For example, U.S. Pat. No. 3,328,449 discloses $(CH_3O)_3Si(CH_2)_3$—$NHCH_2CH_2NHCH_2CH_2CH_2SO_3H$.

However, a compound having an alkoxysilyl group and an alkali metal salt of sulfonic acid or sulfuric acid in a molecule and a hydrophilic polyoxyalkylene chain as a spacer moiety is not known in the art.

SUMMARY OF THE INVENTION

We have found that a novel organic silicon compound of formula (1) having an alkoxy group at one end and an alkali metal salt of sulfuric acid or sulfonic acid at the other end can be obtained by effecting hydrosilylation reaction between an alkoxyhydrosilane compound of formula (2) and a compound of formula (3) having an alkenyl group at one end and an alkali metal salt of sulfuric acid or sulfonic acid at the other end as shown by the following scheme.

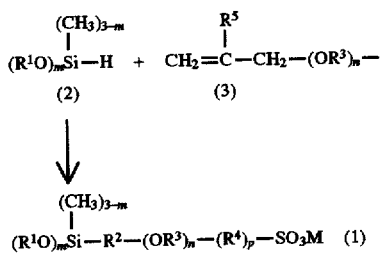

In the formulae, $R^1$ is an alkyl group, $R^2$ is an alkylene group having at least 3 carbon atoms, $R^3$ is an alkylene group having at least 2 carbon atoms, $R^4$ is an oxygen atom or divalent hydrocarbon group containing an oxygen atom, $R^5$ is a hydrogen atom or methyl group, M is an alkali metal, letter m is a number of 1 to 3, n is a number of 3 to 60, and p is equal to 0 or 1.

We have also found that when inorganic material is surface treated with the organic silicon compound of formula (1), that is, alkoxysilane compound having an alkali metal salt of sulfuric acid or sulfonic acid in a molecule, the inorganic material surface can be rendered hydrophilic. Therefore the organic silicon compound of formula (1) is useful as a surface treating agent for inorganic materials and a modifier for composite materials of organic resins and inorganic materials.

Accordingly, the present invention provides an organic silicon compound of formula (1) and a process for preparing an organic silicon compound of formula (1) by effecting hydrosilylation reaction between compounds of formulae (2) and (3).

DETAILED DESCRIPTION OF THE INVENTION

Figure 1:
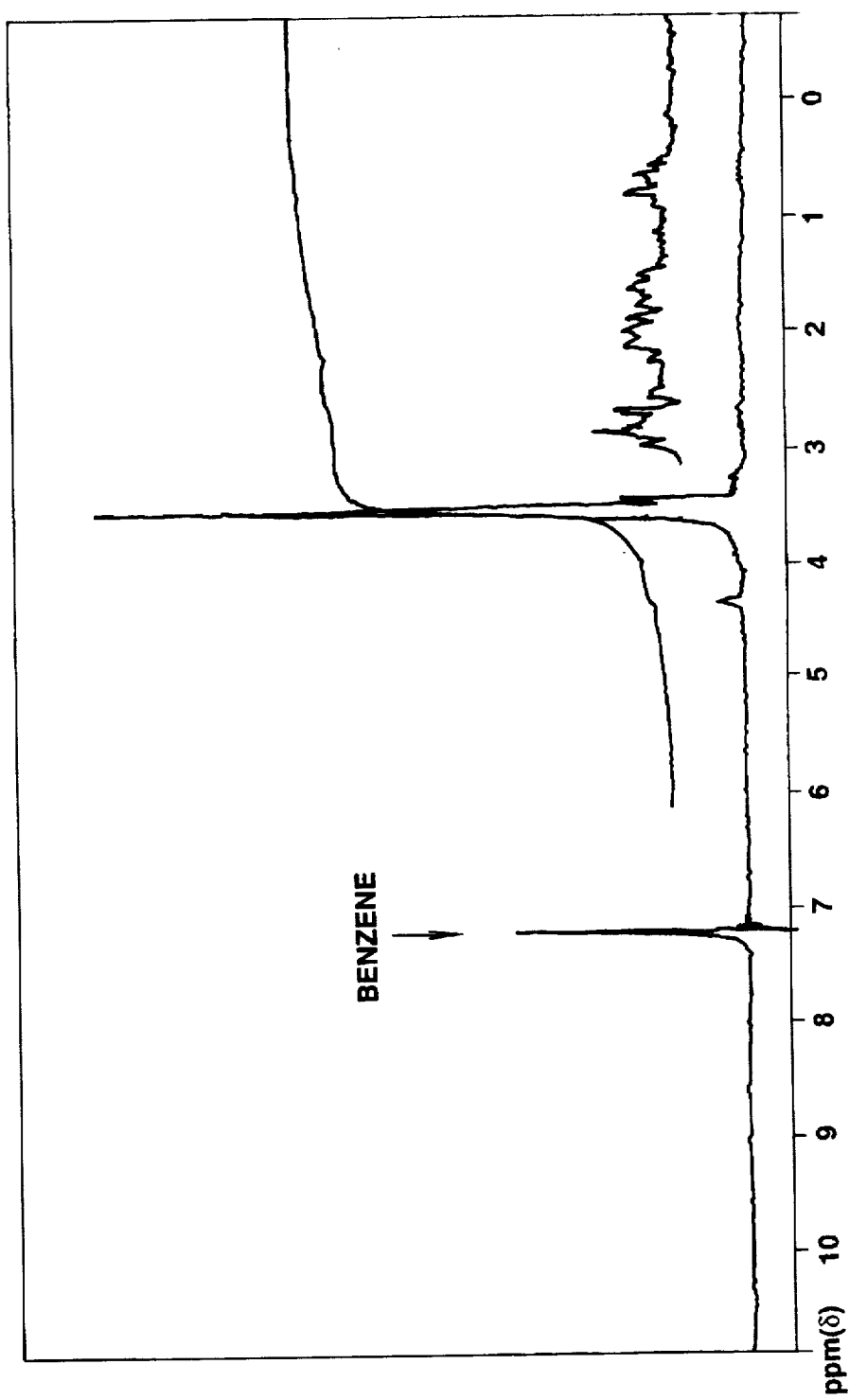
FIGS. 1 and 2 are NMR and IR charts of the compound of Example 1, respectively.

The organic silicon compounds of the present invention are of the following general formula (1).

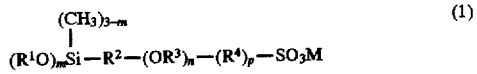

$R^1$ is an alkyl group, $R^2$ is an alkylene group having at least 3 carbon atoms, $R^3$ is an alkylene group having at least 2 carbon atoms, $R^4$ is an oxygen atom or divalent hydrocarbon group containing an oxygen atom, M is an alkali metal, letter m is a number of 1 to 3, n is a number of 3 to 60, and p is equal to 0 or 1.

More particularly, the alkyl group represented by $R^1$ preferably has 1 to 6 carbon atoms, with methyl and ethyl groups being especially preferred. The alkylene group represented by $R^2$ may be either normal or branched and preferably has 3 or 4 carbon atoms, with —$(CH_2)_3$— and —$CH_2CH(CH_3)CH_2$— being especially preferred. The alkylene group represented by $R^3$ may be either normal or branched and preferably has 2 to 4 carbon atoms, especially 2 or 3 carbon atoms, with —$CH_2CH_2$—, —$CH(CH_3)CH_2$— and —$CH_2CH(CH_3)$— being especially preferred. $R^4$ is an oxygen atom or divalent hydrocarbon group, preferably of 1 to 10 carbon atoms, especially 1 to 3 carbon atoms, containing an oxygen atom. Examples include —O—, —$OCH_2$—, —O—$(CH_2)_3$—, —O—$(CH_2)_6$—, —O—$(CH_2)_{10}$—, —$OCH_2O$—, —O—$(CH_2)_3$—O—, —O—$(CH_2)_6$—O—, and —O—$(CH_2)_{10}$—O—. M is an alkali metal such as Na and K. Letter m is a number of 1 to 3, n is a number of 3 to 60, preferably 5 to 30, and p is equal to 0 or 1.

Illustrative, non-limiting examples of the compound of formula (1) are given below.

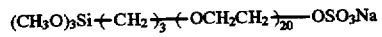

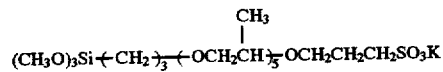

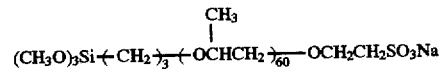

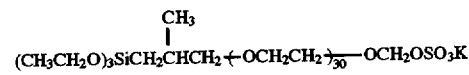

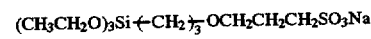

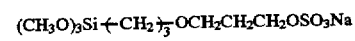

The compound of formula (1) can be readily prepared in high yields by effecting hydrosilylation reaction between a compound of the following formula (2) and a compound of the following formula (3) in the presence of a compound of Group IV transition metal.

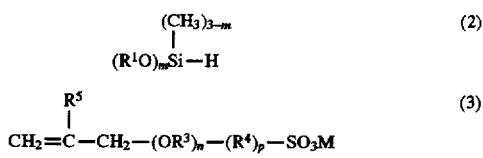

In the formulae, $R^1$, $R^3$, $R^4$, M, m, n and p are as defined above, and $R^5$ is a hydrogen atom or methyl group.

Illustrative examples of the compounds of formulae (2) and (3) are given below.

Exemplary compounds of formula (2)

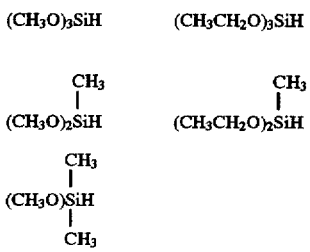

Exemplary compounds of formula (3)

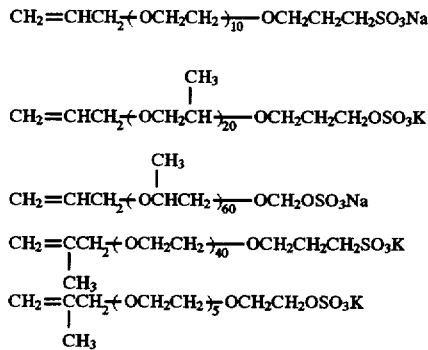

The Group IV transition metal compound used may be selected from well-known catalysts for hydrosilylation, for example, compounds of Pt, Rh, Pd, and Ru, typically chloroplatinic acid.

The compound of formula (2) and the compound of formula (3) may be used in any desired proportion although they are preferably used in a molar ratio between 5:1 and 1:2. The Group IV transition metal compound is used in a catalytic amount, typically about 5 to 2,000 ppm calculated as transition metal atom.

Preferably hydrosilylation reaction is carried out at a temperature of 30° to 150° C. for about 1 to 30 hours. The reaction solvent, if used, is preferably selected from aromatic hydrocarbons such as toluene and xylene, alcohols such as methanol and ethanol, ethers such as tetrahydrofuran, esters such as ethyl acetate, and amides such as dimethylformamide.

It is noted that the compound of formula (3) is commercially available in the trade name of Adeka Carpole LX-1060 (Asahi Denka Kogyo K.K.), for example.

The organic silicon compounds, also defined as alkoxysilanes having a sulfonate group in a molecule, according to the invention will find use as a surface treating agent and modifier. When inorganic material is surface treated with the inventive organic silicon compound, the surface can be rendered hydrophilic. The inventive organic silicon compound is also useful as a modifier for a composite body of an organic resin and an inorganic material.

EXAMPLE

Examples of the present invention are given below by way of illustration and not by way of limitation.

Example 1

Figure 2:
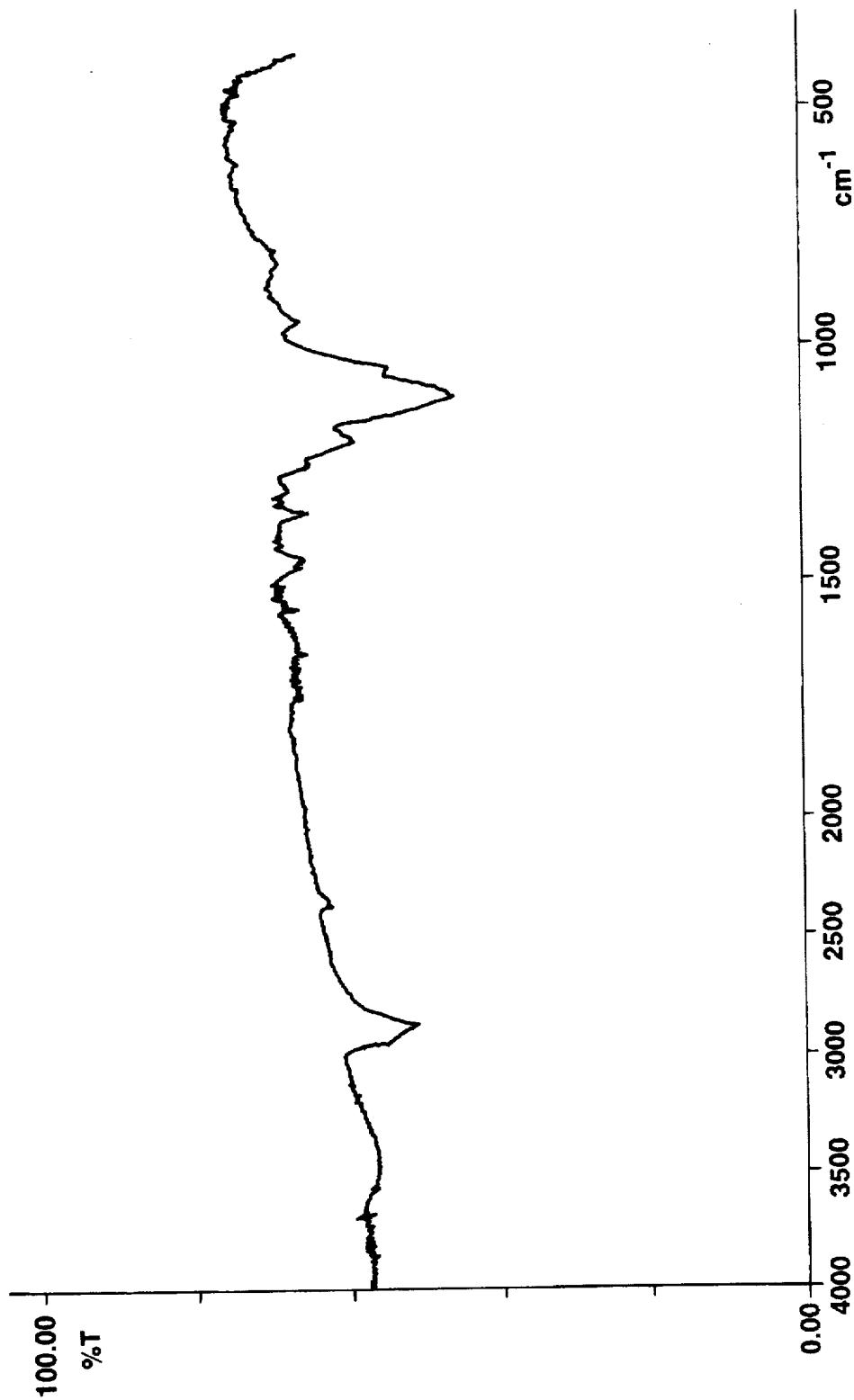

A 1-liter separable flask equipped with a stirrer, thermometer, reflux condenser, and dropping funnel was charged with 149.5 grams (0.25 mol) of a compound of formula (A) shown below and 370 grams of toluene whereupon the contents were dried at 115° C. for 2 hours. The flask was cooled to 70° C. whereupon 2.0 grams of a 2% ethanol solution of chloroplatinic acid was added and 36.6 grams (0.3 mol) of trimethoxysilane was then added dropwise at 70° C. After the completion of dropwise addition, stirring was continued for 20 hours at 80° C. After the completion of reaction, the toluene was distilled off under vacuum at 80° C., yielding 152.8 grams of a brown solid. On analysis by proton nuclear magnetic resonance (NMR) spectroscopy, it was identified to be a compound represented by formula (B) shown below. The yield was 86.8%. FIGS. 1 and 2 are NMR and IR charts of this compound, respectively.

$CH_2=CHCH_2-(OCH_2CH_2)_9-OCH_2CH_2CH_2SO_3Na$ (A)

$(CH_3O)_3Si-(CH_2)_3-OCH_2CH_2)_9-OCH_2CH_2CH_2SO_3Na$ (B)

Examples 2–5

The procedure of Example 1 was repeated using the compounds shown in Table 1. On analysis by $^1H$-NMR spectroscopy and IR absorption spectroscopy, the products were identified to be compounds as shown in Table 1.

TABLE 1

| Example | Compound of formula (2) | Compound of formula (3) | Product |
|---|---|---|---|
| 2 | $(CH_3CH_2O)_3SiH$ | 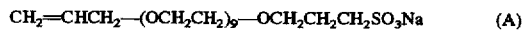 | 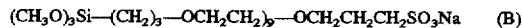 |

TABLE 1-continued

| Example | Compound of formula (2) | Compound of formula (3) | Product |
|---------|------------------------|-------------------------|---------|
| 3 | $(CH_3O)_2SiH$ with $CH_3$ | 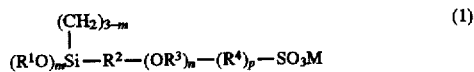 | 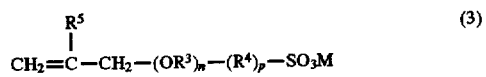 |
| 4 | $(CH_3O)_3SiH$ | $CH_2=CHCH_2+OCH_2CH_2)_{30}$—$OSO_3K$ | $(CH_3O)_3Si+CH_2)_3+OCH_2CH_2)_{30}$—$OSO_3K$ |
| 5 | $(CH_3CH_2O)_2SiH$ with $CH_3$ | 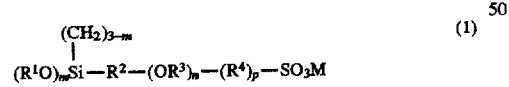 |  |

Japanese Patent Application No. 347893/1995 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. An organic silicon compound of the following general formula (1):

$$(R^1O)_mSi\begin{matrix}(CH_2)_{3-m}\\|\\\end{matrix}-R^2-(OR^3)_n-(R^4)_p-SO_3M \quad (1)$$

wherein $R^1$ is an alkyl group, $R^2$ is an alkylene group having at least 3 carbon atoms, $R^3$ is an alkylene group having at least 2 carbon atoms, $R^4$ is an oxygen atom or divalent hydrocarbon group containing an oxygen atom, M is an alkali metal, letter m is a number of 1 to 3, n is a number of 3 to 60, and p is equal to 0 or 1.

2. A process for preparing an organic silicon compound of the following formula (1):

$$(R^1O)_mSi\begin{matrix}(CH_2)_{3-m}\\|\\\end{matrix}-R^2-(OR^3)_n-(R^4)_p-SO_3M \quad (1)$$

wherein $R^1$ is an alkyl group, $R^2$ is an alkylene group having at least 3 carbon atoms, $R^3$ is an alkylene group having at least 2 carbon atoms, $R^4$ is an oxygen atom or divalent hydrocarbon group containing an oxygen atom, M is an alkali metal, letter m is a number of 1 to 3, n is a number of 3 to 60, and p is equal to 0 or 1, said process comprising the step of effecting hydrosilylation reaction between a compound of the following formula (2):

$$(R^1O)_mSi\begin{matrix}(CH_3)_{3-m}\\|\\\end{matrix}-H \quad (2)$$

wherein $R^1$ and m are as defined above and a compound of the following formula ( 3):

$$\begin{matrix}R^5\\|\\CH_2=C-CH_2-(OR^3)_n-(R^4)_p-SO_3M\end{matrix} \quad (3)$$

wherein $R^3 R^4$, M, n and p are as defined above, and $R^5$ is a hydrogen atom or methyl group.

3. The organic silicon compound of claim 1, wherein $R^1$ is an alkyl group of 1–6 carbon atoms, $R^2$ is an alkylene group of 3 or 4 carbon atoms, $K^3$ is an alkylene group of 2 to 4 carbon atoms, $R^4$ is an oxygen atom or divalent hydrocarbon group containing an oxygen atom and 1 to 10 carbon atoms.

4. The organic silicon compound of claim 1, wherein M is Na or K.

5. The organic silicon compound of claim 1, which is of one of the following formulae:

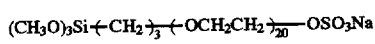

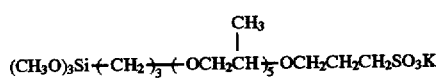

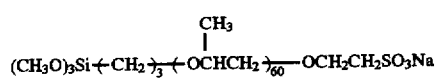

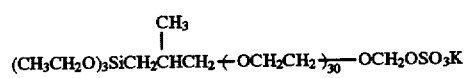

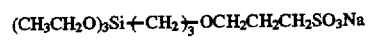

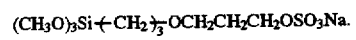

6. The process of claim 2, wherein $R^1$ is an alkyl group of 1–6 carbon atoms, $R^2$ is an alkylene group of 3 or 4 carbon atoms, $R^3$ is an alkylene group of 2 to 4 carbon atoms, $R^4$ is an oxygen atom or divalent hydrocarbon group containing an oxygen atom and 1 to 10 carbon atoms.

7. The process of claim 2, wherein M is Na or K.

8. The process of claim 2, wherein the hydrosilylation reaction is effected in the presence of a Group IV transition metal compound.

9. The process of claim 2, wherein the compound of formula (2) and the compound of formula (3) are reacted in a molar ratio between 5:1 and 1:2.

10. The process of claim 2, wherein the hydrosilylation reaction is effected at a temperature of 30° to 150° C. for about 1 to 30 hours.

* * * * *